United States Patent [19]

Jennison

[11] 4,091,675
[45] May 30, 1978

[54] SAMPLERS

[75] Inventor: William Jennison, Thurso, Scotland

[73] Assignee: United Kingdom Atomic Energy Authority, England

[21] Appl. No.: 755,242

[22] Filed: Dec. 29, 1976

Related U.S. Application Data

[63] Continuation of Ser. No. 551,080, Feb. 20, 1975, abandoned.

[30] Foreign Application Priority Data

Mar. 8, 1974 United Kingdom ............... 10609/74

[51] Int. Cl.² ............................................. G01N 1/14
[52] U.S. Cl. ................................. 73/422 R; 73/421 B; 73/304 C

[58] Field of Search .......... 73/422 R, 421 B, 425.4 R, 73/304 C, 422 TC; 137/392

[56] References Cited

U.S. PATENT DOCUMENTS

| 3,719,081 | 3/1973 | Lynn et al. ..................... 73/422 R |
| 3,821,900 | 7/1974 | Preikschat ........................ 73/304 C |

Primary Examiner—Richard E. Aegerter
Assistant Examiner—Willis Little
Attorney, Agent, or Firm—Larson, Taylor and Hinds

[57] ABSTRACT

A sampler for taking samples continuously, at a rate proportional to flow, in which the head of liquid is sensed by capacitor probes and a voltage is generated for driving a stepping motor, the stepping motor being used to operate a pump controlling sampling.

2 Claims, 1 Drawing Figure

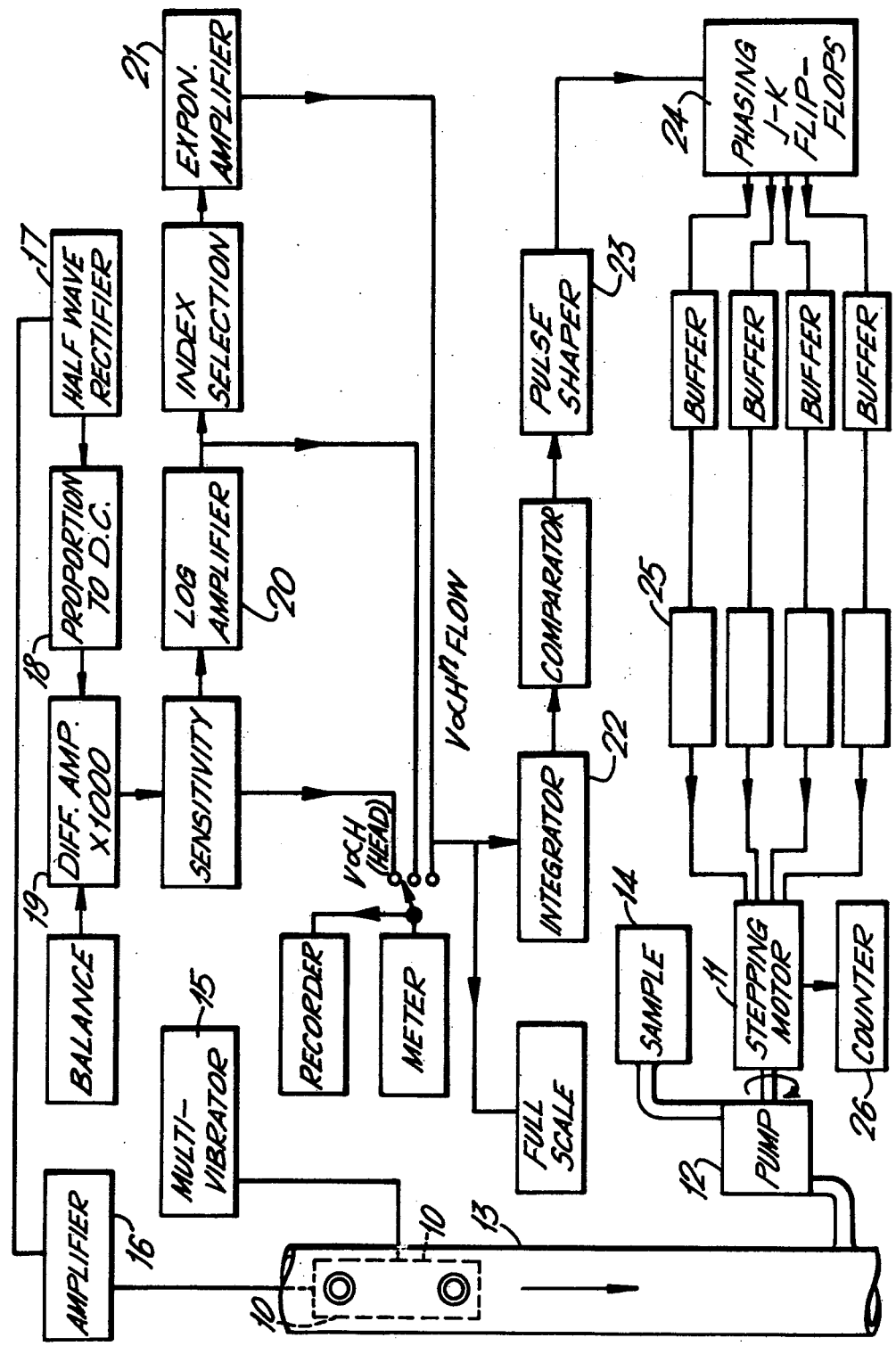

SAMPLERS

This is a continuation, of application Ser. No. 551,080 filed Feb. 20, 1975. Now abandoned.

BACKGROUND OF THE INVENTION

This invention relates to samplers for sampling the flow of liquid in a pipe or drain and it has one important application to the sampling of effluent either because that effluent may contain a valuable product or because it may involve a pollution hazard.

In general, process pipes or drains may carry products at widely differing rates. In order to account for and measure such products a representative sample having a volume proportional to flow is required for analysis. Devices for taking such samples are referred to as liquid flow proportional samplers and two such devices are described in a report numbered TRG 2163 D by W Jennison and available from HM Stationery Office. The present invention is an improvement of a capacitative probe device disclosed in said report.

SUMMARY OF THE INVENTION

A liquid flow proportional sampler according to the present invention comprises an insulated electrode capable of being inserted in a flowing liquid and a further electrode forming with the first-mentioned electrode a capacitor with an electrical output which is dependent on the depth of insertion of the electrodes in the flowing liquid; a stepping motor driven pump for taking a sample volume from the liquid; means for alternately charging and discharging the capacitance between the electrodes; means for converting the charging current into a voltage analogue; means for raising said voltage analogue to a predetermined power index correlating the depth of insertion of the electrodes and the pressure head of the flowing liquid to give a flow analogue; and means for converting said flow analogue into a pulse train to operate said stepping motor so that said pump takes from the flowing liquid a sample volume proportional to the flow of liquid.

The sampler as above stated can be formed so as to be readily insertable into a pipe or drain and operates in flow channels with and without weirs.

In the case of a liquid in a well earthed conducting pipe the sampler becomes effectively a single insulated probe electrode arrangement. The capacitance measured then stems, in effect, from a form of coaxial capacitor. If a liquid is isolated from earth (because, for example, it is flowing in a non-conducting channel) an earth probe may be inserted. If non-conducting liquid is having its flow measured and the impedance of the path to earth is greater than about 50Kohms (depending on other parameters) a second probe becomes essential. In the general case, and with a partially immersed electrode, two capacitances in parallel are set up between the electrodes. One has an air dielectric and the other a liquid dielectric and the overall capacitance change tends to be a linear function of the depth of immersion.

The predetermined power index referred to above is dependent on the form of flow channel in use and whether it includes a weir or not, and the form of weir where one is provided. Typically the power is 1.5 for a rectangular notch weir or rectangular open channel; 2.5 for a triangular weir; 2.0 for a semi-circular open channel; or 1.7 for circular pipe flow. These figures are not precise and for true precision would have to change slightly for certain modifying features such as extremes of flow rates.

Typical electrodes comprise rods or tubes of circular section, for example, a copper tube inside a polyethylene sleeve or for small flow channels, a hypodermic needle with a PTFE coating. In general, the insulation on the electrodes should be not wettable by the liquid in which they are to be immersed as otherwise the wetted level tends to represent itself as the immersion depth.

Electrode spacing is not critical and this feature permits one electrode to be spaced considerably downstream of the other if required.

DESCRIPTION OF THE DRAWING

The invention will now be further described with reference to the accompanying drawing which is a block schematic circuit diagram.

DESCRIPTION OF A PREFERRED EMBODIMENT

Block 10 represents spaced insulated electrodes for immersion in a liquid in a pipe 13. Block 11 is a stepping motor for driving a peristaltic pump 12 by which a proportional sample is taken from the pipe 13 downstream of electrodes 10 and deposited in a sample container 14. Block 15 is a multivibrator and amplitude limiter for alternately charging and discharging the electrodes 10 at, for example 15KHz. The charging current from the electrodes 10 is amplified at block 16 and half-wave rectified at block 17. A voltage analogue is derived at block 18, amplified at block 19 and balanced at zero level of liquid (i.e. zero flow) in the pipe 13. The analogue is raised to the required index by a logarithmic amplifier block 20 and an exponential amplifier block 21 and is converted to a pulse train by a block 22 from whence it passes to a pulse shaper block 23 to feed phasing flip-flops 24, which in turn feeds pulses to current amplifiers 25 and to the four phases of stepping motor 11. The motor has a counter 26 for measuring sample volume.

Other control, setting up and ancillary blocks are also shown and identified but not specifically described.

The electrodes 10 can readily be inserted in a pipe by drilling holes in the top of the pipe and inserting the circular section electrodes.

The sampler above described can, for the most part, use digital and linear integrated circuits of very low cost. The derived flow analogue is substantially independent of dissolved compounds. The circuits can be assembled on two printed circuit boards which are mounted on both sides of a thermostated aluminium plate and enclosed in a case. The multivibrator 15 and amplifier 16 are placed close to the electrodes 10 to minimise lead capacitance. Connections to the control circuit can be over longer leads.

The counter 26 may be operated from a reed relay switch responsive to a magnet secured to rotate with the shaft between stepping motor and pump. Typically full flow in the pipe is represented by 100 RPM at the motor and twentyfive revolutions cause a 1ml sample to be taken. Thus the mean percent flow over a period of time can be derived by dividing the change in counter reading by elapsed time in minutes.

We claim:

1. A liquid proportional sampler comprising an insulated electrode capable of being inserted in a flowing liquid and a further electrode forming with the first-mentioned electrode a capacitor with an electrical output which is dependent on the depth of insertion of the electrodes in the flowing liquid; a stepping motor driven pump for continuously taking a sample volume from the liquid; means connected to said electrodes for alternately charging and discharging the capacitance between the electrodes; means connected to said electrodes for converting the charging current of said electrodes into a voltage analogue; means connected to said converting means for raising said voltage analogue to a predetermined power index correlating the depth of insertion of the electrodes and the pressure head of the flowing liquid to produce a flow analogue signal; and means for converting said flow analogue signal into a pulse train to operate the stepping motor so that said pump takes from the flowing liquid a sample volume proportional to the flow of liquid, said means for raising said voltage analogue comprising a logarithmic amplifier and an exponential amplifier and said power index being greater than 1.0 and less than 2.5.

2. A liquid proportional sampler as claimed in claim 1 wherein the first-mentioned electrode and the further electrode can be inserted together into liquid flowing in a pipe through a single hole in the pipe.

* * * * *